(12) United States Patent
Nakano et al.

(10) Patent No.: US 10,288,579 B2
(45) Date of Patent: May 14, 2019

(54) GAS SENSOR

(71) Applicant: NGK Spark Plug Co., LTD., Nagoya (JP)

(72) Inventors: Yoshihiro Nakano, Komaki (JP); Tetsuo Yamada, Komaki (JP)

(73) Assignee: NGK SPARK PLUG CO., LTD., Nagoya (JP)

( * ) Notice: Subject to any disclaimer, the term of this patent is extended or adjusted under 35 U.S.C. 154(b) by 87 days.

(21) Appl. No.: 15/426,737

(22) Filed: Feb. 7, 2017

(65) Prior Publication Data

US 2017/0227490 A1   Aug. 10, 2017

(30) Foreign Application Priority Data

Feb. 9, 2016 (JP) .................. 2016-022861
Feb. 2, 2017 (JP) .................. 2017-017453

(51) Int. Cl.
*G01N 27/407* (2006.01)
*G01N 33/00* (2006.01)

(52) U.S. Cl.
CPC ..... *G01N 27/4072* (2013.01); *G01N 27/4076* (2013.01); *G01N 33/0054* (2013.01)

(58) Field of Classification Search
CPC ............. G01N 27/406; G01N 27/4071; G01N 33/0054
See application file for complete search history.

(56) References Cited

U.S. PATENT DOCUMENTS 4,282,080 A * 8/1981 Muller ............... G01N 27/4067
                                                      204/412
4,300,990 A * 11/1981 Maurer ............... G01N 27/4071
                                                      204/412

FOREIGN PATENT DOCUMENTS

JP          2013-221930 A     10/2013

* cited by examiner

*Primary Examiner* — Alexander S Noguerola
(74) *Attorney, Agent, or Firm* — Leason Ellis LLP (57) ABSTRACT

An ammonia detection section is disposed on an electrically insulating layer and includes a reference electrode, a solid electrolyte body for ammonia, and a detection electrode that are stacked in this order on the electrically insulating layer. In the ammonia detection section, a three-phase boundary is formed at the interface between the reference electrode and the solid electrolyte body for ammonia, and another three-phase boundary is formed at the interface between the detection electrode and the solid electrolyte body for ammonia. The concentration of ammonia in exhaust gas is thereby detected. The ammonia detection section includes a porous layer formed of an electrically insulating porous material and disposed between the insulating layer and the reference electrode.

9 Claims, 5 Drawing Sheets

GAS SENSOR

This application claims the benefit of Japanese Patent Applications No. 2016-022861, filed Feb. 9, 2016 and No. 2017-017453, filed Feb. 2, 2017, all of which are incorporated by reference herein in its entirety.

FIELD OF THE INVENTION

The present invention relates to a gas sensor that detects the concentration of a gas present in an atmosphere of interest.

BACKGROUND OF THE INVENTION

In recent years, a urea SCR (Selective Catalytic Reduction) system is receiving attention as a technique for cleaning NOx-containing exhaust gas emitted from internal combustion engines such as gasoline engines and diesel engines (where NOx stands for nitrogen oxides). In the urea SCR system, ammonia ($NH_3$) is chemically reacted with nitrogen oxides (NOx) to reduce the nitrogen oxides to nitrogen ($N_2$), and the exhaust gas containing the nitrogen oxides is thereby cleaned.

In the urea SCR system, when the amount of ammonia supplied for the nitrogen oxides is excessively large, unreacted ammonia may be contained in the exhaust gas and emitted to the outside. To reduce the emission of ammonia described above, a multi-gas sensor capable of measuring the concentrations of a plurality of gases including ammonia contained in the exhaust gas is used for the urea SCR system.

In one known multi-gas sensor, an ammonia sensor including a reference electrode, a detection electrode, and a solid electrolyte body sandwiched between these electrodes is attached to an NOx sensor (see, for example, Japanese Patent Application Laid-Open (kokai) No. 2013-221930).

Problems to be Solved by the Invention

When a stack of the reference electrode and the solid electrolyte body is formed on a green insulating layer provided on the uppermost surface of the NOx sensor and then they are co-fired, the insulating layer provided on the uppermost surface of the NOx sensor shrinks. In this case, the reference electrode becomes dense, and the area of a three-phase boundary is reduced, so that the impedance of the ammonia sensor rises. When the impedance rises, the output of the ammonia sensor is easily influenced by noise, so that the detection accuracy of the ammonia sensor may be reduced significantly.

The present invention has been made in view of the above problem, and it is an object to provide a technique for suppressing the rise in impedance due to co-firing.

SUMMARY OF THE INVENTION

Means for Solving the Problems

A first aspect of the present invention accomplished to achieve the above-described object is a gas sensor disposed on an electrically insulating member for detecting the concentration of a target gas in an atmosphere of interest. The gas sensor comprises a reference electrode, a solid electrolyte body, and a detection electrode that are stacked in this order on the electrically insulating member, a first three-phase boundary being formed at a first interface between the reference electrode and the solid electrolyte body, a second three-phase boundary being formed at a second interface between the detection electrode and the solid electrolyte body. The atmosphere of interest is a gas atmosphere to be detected by the gas sensor. Each three-phase boundary is a boundary at which the target gas comes into contact with the solid electrolyte body and one of the reference electrode and the detection electrode.

The gas sensor according to the first aspect of the present invention further comprises an insulating porous layer made of an electrically insulating porous material and disposed between the electrically insulating member and the reference electrode.

In the above-configured gas sensor of the first aspect, the insulating porous layer is disposed on the opposite side of the reference electrode from the solid electrolyte body. The insulating porous layer has many pores in its interior and on its surface. Therefore, in the insulating porous layer, the detection target gas is allowed to flow from a portion exposed to the atmosphere of interest into the interior of the insulating porous layer, and the target gas flowing inside the insulating porous layer is allowed to flow toward the reference electrode.

Therefore, the amount of the target gas flowing through the reference electrode toward the solid electrolyte body increases, and this allows an increase in the area of the three-phase boundary at which the detection target gas comes into contact with the reference electrode and the solid electrolyte body. When a stack of the reference electrode and the solid electrolyte body is formed on a green electrically insulating member and then they are co-fired, the reference electrode may become dense, and the area of the three-phase boundary may decrease. Even in this case, the increase in the inflow of the target gas through the insulating porous layer allows the reduction in the area of the three-phase boundary to be suppressed.

By virtue of the above-described configuration, the gas sensor of the first aspect of the present invention can suppress the rise in the impedance of the gas sensor due to co-firing.

A second aspect of the present invention accomplished to achieve the above-described object is a gas sensor disposed on an electrically insulating member for detecting the concentration of a target gas in an atmosphere of interest. The gas sensor comprises a reference electrode, a solid electrolyte body, and a detection electrode that are stacked in this order on the electrically insulating member, a first three-phase boundary being formed at a first interface between the reference electrode and the solid electrolyte body, a second three-phase boundary being formed at a second interface between the detection electrode and the solid electrolyte body.

In the gas sensor according to the second aspect of the present invention, at least part of the solid electrolyte body is porous and abuts the reference electrode.

In the above-configured gas sensor of the second aspect, the porous part of the solid electrolyte body is disposed between the non-porous part of the solid electrolyte body and the reference electrode. Therefore, in the porous part of the solid electrolyte body, the target gas is allowed to flow from a portion exposed to the atmosphere of interest into the interior of the porous part of the solid electrolyte body, and the target gas flowing inside the porous part of the solid electrolyte body is allowed to flow toward the reference electrode.

Therefore, the amount of the target gas flowing through the solid electrolyte body toward the reference electrode increases, and this allows an increase in the area of the three-phase boundary at which the target gas comes into contact with the reference electrode and the solid electrolyte body. When a stack of the reference electrode and the solid electrolyte body is formed on a green electrically insulating member and then they are co-fired, the reference electrode may become dense, and the area of the three-phase boundary may decrease. Even in this case, the increase in the inflow of the target gas through the porous part of the solid electrolyte body allows the reduction in the area of the three-phase boundary to be suppressed.

By virtue of the above-described configuration, the gas sensor of the second aspect of the present invention can suppress the rise in the impedance of the gas sensor due to co-firing.

BRIEF DESCRIPTION OF THE DRAWINGS

These and other features and advantages of the present invention will become more readily appreciated when considered in connection with the following detailed description and appended drawings, wherein like designations denote like elements in the various views, and wherein.

DETAILED DESCRIPTION OF THE INVENTION

Modes for Carrying Out the Invention

First Embodiment

An embodiment of the present invention will be described with reference to the drawings.

A multi-gas detector 1 in the embodiment to which the present invention is applied is used for a urea SCR (Selective Catalytic Reduction) system that is mounted on a vehicle to thereby clean nitrogen oxide (NOx)-contained exhaust gas emitted from a diesel engine. More specifically, the multi-gas detector 1 measures, after the NOx contained in the exhaust gas is reacted with ammonia (urea), the concentrations of nitrogen monoxide (NO), nitrogen dioxide ($NO_2$), and ammonia contained in the resulting exhaust gas. The vehicle on which the multi-gas detector 1 is mounted is referred to as the "present vehicle."

Figure 1:
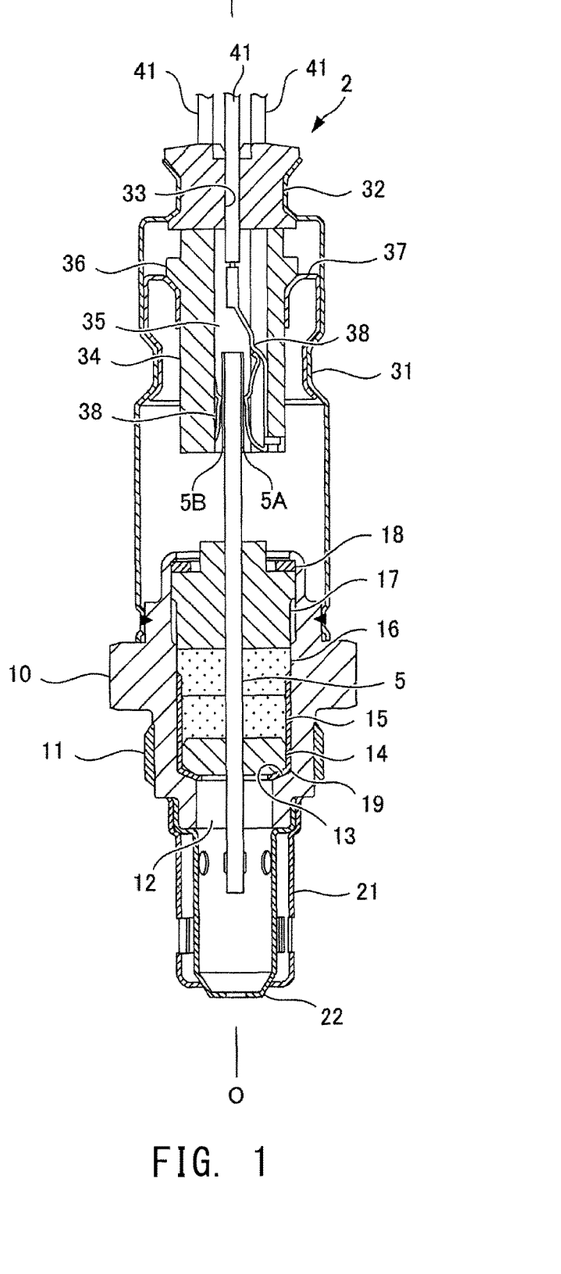
FIG. 1 is a cross-sectional view showing the internal structure of a multi-gas sensor 2.
Figure 2:
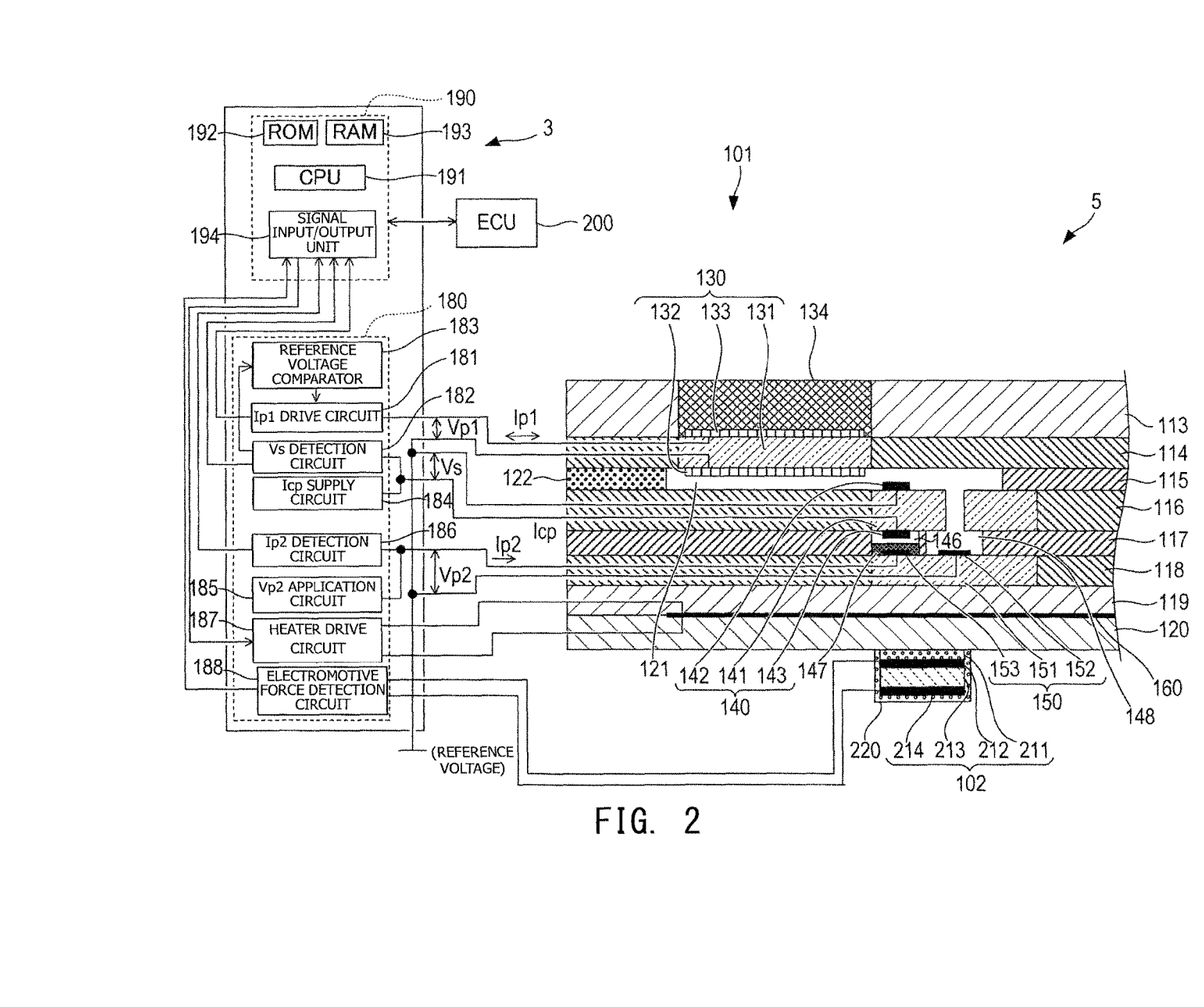
FIG. 2 is an illustration showing the schematic configuration of a sensor element unit 5 and a controller 3 in a first embodiment.

The multi-gas detector 1 includes a multi-gas sensor 2 shown in FIG. 1 and a controller 3 shown in FIG. 2.

As shown in FIG. 1, the multi-gas sensor 2 includes a sensor element unit 5, a metallic shell 10, a separator 34, and connection terminals 38. In the following description, the side of the multi-gas sensor 2 on which the sensor element unit 5 is disposed (the lower side in FIG. 1) is referred to as a forward end side, and the side on which the connection terminals 38 are disposed (the upper side in FIG. 1) is referred to as a rear end side.

The sensor element unit 5 has a plate shape extending in the direction of an axial line O. Electrode terminal portions 5A and 5B are disposed at the rear end of the sensor element unit 5. In FIG. 1, only the electrode terminal portions 5A and 5B are shown as electrode terminal portions formed in the sensor element unit 5 for the purpose of simplifying the drawing. However, in practice, a plurality of electrode terminal portions are formed according to the number of, for example, electrodes included in an NOx detection section 101 and an ammonia detection section 102 described later.

The metallic shell 10 is a tubular member, and a threaded portion 11 used to fix the multi-gas sensor 2 to an exhaust pipe of a diesel engine is formed on the external surface of the metallic shell 10. The metallic shell 10 has a through hole 12 extending in the direction of the axial line O and a ledge 13 protruding inward in the radial direction of the through hole 12. The ledge 13 is formed as an inward tapered surface extending from the radially outer side of the through hole 12 toward its center and inclined toward the forward end side.

The metallic shell 10 holds the sensor element unit 5 with its forward end protruding from the forward end of the through hole 12 and the rear end protruding from the rear end of the through hole 12.

A ceramic holder 14 that is a tubular member surrounding the radial circumference of the sensor element unit 5, talc rings 15 and 16 that are powder filler layers, and a ceramic sleeve 17 are stacked in this order inside the through hole 12 of the metallic shell 10 from the forward end side toward the rear end side.

A crimp packing 18 is disposed between a rear end portion of the ceramic sleeve 17 and a rear end portion of the metallic shell 10. A metallic holder 19 is disposed between the ceramic holder 14 and the ledge 13 of the metallic shell 10. The metallic holder 19 holds the talc ring 15 and the ceramic holder 14. A rear end portion of the metallic shell 10 is crimped so as to press the ceramic sleeve 17 toward the forward end side through the crimp packing 18.

An outer protector 21 and an inner protector 22 are disposed at a forward end portion of the metallic shell 10. The outer protector 21 and the inner protector 22 are tubular members formed from a metallic material such as stainless steel having a closed forward end. The inner protector 22 covers a forward end portion of the sensor element unit 5 and is welded to the metallic shell 10, and the outer protector 21 covers the inner protector 22 and is welded to the metallic shell 10.

A forward end portion of an outer tube 31 formed into a tubular shape is fixed to a rear end portion of the metallic shell 10. A grommet 32 is disposed in a rear end opening of the outer tube 31 so as to close the opening.

Lead wire insertion holes 33 into which lead wires 41 are inserted are formed in the grommet 32. The lead wires 41 are electrically connected to the electrode terminal portions 5A and 5B of the sensor element unit 5.

A separator 34 is a tubular member disposed rearward of the sensor element unit 5. A space formed inside the separator 34 is an insertion hole 35 passing through the separator 34 in the direction of the axial line O. A flange portion 36 protruding radially outward is formed on the outer surface of the separator 34.

A rear end portion of the sensor element unit 5 is inserted into the insertion hole 35 of the separator 34, and the electrode terminal portions 5A and 5B are disposed inside the separator 34.

A tubular holding member 37 is disposed between the separator 34 and the outer tube 31. The holding member 37 is in contact with the flange portion 36 of the separator 34 and also with the inner surface of the outer tube 31 and thereby holds the separator 34 such that the separator 34 is fixed to the outer tube 31.

The connection terminals 38 are members disposed inside the insertion hole 35 of the separator 34 and are electrically conductive members that electrically connect the electrode terminal portions 5A and 5B of the sensor element unit 5 to their respective lead wires 41. In FIG. 1, only two connection terminals 38 are shown for the purpose of simplifying the drawing.

As shown in FIG. 2, a controller 3 of the multi-gas detector 1 is electrically connected to an electronic control unit 200 mounted on the present vehicle. The electronic control unit 200 receives data representing the concentrations of NO, $NO_2$, and ammonia in exhaust gas that are computed by the controller 3. Then the electronic control unit 200 performs processing for controlling the operating conditions of the diesel engine according to the data received and also performs cleaning processing for NOx accumulated on a catalyst.

The sensor element unit 5 includes the NOx detection section 101 and the ammonia detection section 102.

The NOx detection section 101 is formed by sequentially stacking an insulating layer 113, a ceramic layer 114, an insulating layer 115, a ceramic layer 116, an insulating layer 117, a ceramic layer 118, an insulating layer 119, and an insulating layer 120. The insulating layers 113, 115, 117, 119, and 120 are formed mainly of alumina.

The NOx detection section 101 includes a first measurement chamber 121 formed between the ceramic layer 114 and the ceramic layer 116. In the NOx detection section 101, the exhaust gas is introduced from the outside into the interior of the first measurement chamber 121 through a diffusion resistor 122 that is disposed between the ceramic layer 114 and the ceramic layer 116 so as to be adjacent to the first measurement chamber 121. The diffusion resistor 122 is formed of a porous material such as alumina.

The NOx detection section 101 further includes a first pumping cell 130. The first pumping cell 130 includes a solid electrolyte layer 131 and pumping electrodes 132 and 133.

The solid electrolyte layer 131 is formed mainly of zirconia having oxygen ion conductivity. A part of the ceramic layer 114 is removed from a region exposed to the first measurement chamber 121, and the resulting space is filled with the solid electrolyte layer 131 instead of the ceramic layer 114.

The pumping electrodes 132 and 133 are formed mainly of platinum. The pumping electrode 132 is disposed on the solid electrolyte layer 131 so as to be exposed to the first measurement chamber 121. The pumping electrode 133 is disposed on the solid electrolyte layer 131 on the side opposite the pumping electrode 132 with the solid electrolyte layer 131 sandwiched between the pumping electrodes 132 and 133. The insulating layer 113 is removed from a region in which the pumping electrode 133 is disposed and from a region around the pumping electrode 133, and the resulting space is filled with a porous material 134 instead of the insulating layer 113. The porous material 134 allows gas (oxygen) migration between the pumping electrode 133 and the outside.

The NOx detection section 101 further includes an oxygen concentration detection cell 140. The oxygen concentration detection cell 140 includes a solid electrolyte layer 141, a detection electrode 142, and a reference electrode 143.

The solid electrolyte layer 141 is formed mainly of zirconia having oxygen ion conductivity. A part of the ceramic layer 116 is removed from a region rearward of the solid electrolyte layer 131, and the resulting space is filled with the solid electrolyte layer 141 instead of the ceramic layer 116.

The detection electrode 142 and the reference electrode 143 are formed mainly of platinum. The detection electrode 142 is disposed on the solid electrolyte layer 141 so as to be exposed to the first measurement chamber 121. The reference electrode 143 is disposed on the solid electrolyte layer 141 on the side opposite the detection electrode 142 with the solid electrolyte layer 141 sandwiched between the detection electrode 142 and the reference electrode 143.

The NOx detection section 101 further includes a reference oxygen chamber 146. The reference oxygen chamber 146 is a through hole formed by removing the insulating layer 117 from a region in which the reference electrode 143 is disposed and from a region around the reference electrode 143.

The NOx detection section 101 further includes a second measurement chamber 148. The second measurement chamber 148 is formed rearward of the detection electrode 142 and the reference electrode 143 so as to pass through the solid electrolyte layer 141 and the insulating layer 117. In the NOx detection section 101, the exhaust gas discharged from the first measurement chamber 121 is introduced into the second measurement chamber 148.

The NOx detection section 101 further includes a second pumping cell 150. The second pumping cell 150 includes a solid electrolyte layer 151 and pumping electrodes 152 and 153.

The solid electrolyte layer 151 is formed mainly of zirconia having oxygen ion conductivity. The ceramic layer 118 is removed from a region exposed to the reference oxygen chamber 146 and the second measurement chamber 148 and a region around this exposed region, and the resulting space is filled with the solid electrolyte layer 151 instead of the ceramic layer 118.

The pumping electrodes 152 and 153 are formed mainly of platinum. The pumping electrode 152 is disposed on the solid electrolyte layer 151 so as to be exposed to the second measurement chamber 148. The pumping electrode 153 is disposed on the solid electrolyte layer 151 so as to be opposed to the reference electrode 143 with the reference oxygen chamber 146 therebetween. A porous material 147 is disposed inside the reference oxygen chamber 146 so as to cover the pumping electrode 153.

The NOx detection section 101 further includes a heater 160. The heater 160 is a heat-generating resistor that is formed mainly of platinum and generates heat when energized and is disposed between the insulating layers 119 and 120.

The ammonia detection section 102 is formed on the outer surface of the NOx detection section 101, more specifically on the insulating layer 120. The ammonia detection section 102 is disposed at substantially the same position, with respect to the direction of the axial line O (the horizontal direction in FIG. 2), as the reference electrode 143 in the NOx detection section 101.

The ammonia detection section 102 has a structure formed by stacking a porous layer 211, a reference electrode 212, a solid electrolyte body 213 for ammonia, and a detection electrode 214 in this order.

The porous layer 211 is formed of the same material as the material of the porous material 134 and is disposed in contact with the surface of the insulating layer 120.

The reference electrode 212 is formed mainly of platinum (Pt) serving as an electrode material and more specifically formed of a material containing Pt and zirconium oxide ($ZrO_2$). The solid electrolyte body 213 for ammonia is formed of an oxygen ion-conductive material such as yttria-stabilized zirconia (YSZ). The reference electrode 212 is a dense layer having a smaller porosity than the porous layer 211. The detection electrode 214 is formed mainly of gold (Au) serving as an electrode material and more specifically formed of a material containing Au and zirconium oxide ($ZrO_2$).

Therefore, a three-phase boundary at which ammonia comes into contact with the reference electrode 212 and the solid electrolyte body 213 for ammonia is formed at the interface between the reference electrode 212 and the solid electrolyte body 213 for ammonia. Similarly, another three-phase boundary at which ammonia comes into contact with the detection electrode 214 and the solid electrolyte body 213 for ammonia is formed at the interface between the detection electrode 214 and the solid electrolyte body 213 for ammonia.

The entire ammonia detection section 102 is covered with a porous protecting layer 220. The protecting layer 220 is configured to prevent adhesion of a poisoning material to the detection electrode 214 and to control the diffusion rate of ammonia flowing from the outside into the ammonia detection section 102.

The controller 3 includes a control circuit 180 and a microcomputer 190.

The control circuit 180 is an analog circuit disposed on a circuit board. The control circuit 180 includes an Ip1 drive circuit 181, a Vs detection circuit 182, a reference voltage comparator 183, an Icp supply circuit 184, a Vp2 application circuit 185, an Ip2 detection circuit 186, a heater drive circuit 187, and an electromotive force detection circuit 188.

The pumping electrode 132, the detection electrode 142, and the pumping electrode 152 are connected to a reference potential. The pumping electrode 133 is connected to the Ip1 drive circuit 181. The reference electrode 143 is connected to the Vs detection circuit 182 and the Icp supply circuit 184. The pumping electrode 153 is connected to the Vp2 application circuit 185 and the Ip2 detection circuit 186. The heater 160 is connected to the heater drive circuit 187.

The Ip1 drive circuit 181 applies a voltage Vp1 between the pumping electrode 132 and the pumping electrode 133 to supply a first pumping current Ip1 and detects the supplied first pumping current Ip1.

The Vs detection circuit 182 detects the voltage Vs between the detection electrode 142 and the reference electrode 143 and outputs the detection result to the reference voltage comparator 183.

The reference voltage comparator 183 compares a reference voltage (e.g., 425 mV) with the output from the Vs detection circuit 182 (the voltage Vs) and outputs the comparison result to the Ip1 drive circuit 181. The Ip1 drive circuit 181 controls the direction and magnitude of the first pumping current Ip1 such that the voltage Vs becomes equal to the reference voltage to thereby adjust the concentration of oxygen in the first measurement chamber 121 to a prescribed value at which decomposition of NOx does not occur.

The Icp supply circuit 184 causes a weak current Icp to flow between the detection electrode 142 and the reference electrode 143. Oxygen is thereby fed from the first measurement chamber 121 to the reference oxygen chamber 146 through the solid electrolyte layer 141, and the concentration of oxygen in the reference oxygen chamber 146 is set to be a prescribed oxygen concentration serving as a reference.

The Vp2 application circuit 185 applies a constant voltage Vp2 (e.g., 450 mV) between the pumping electrode 152 and the pumping electrode 153. In the second measurement chamber 148, NOx is dissociated (reduced) through the catalytic action of the pumping electrodes 152 and 153 included in the second pumping cell 150. The oxygen ions obtained as a result of the dissociation migrate in the solid electrolyte layer 151 between the pumping electrode 152 and the pumping electrode 153, so that a second pumping current Ip2 flows. The Ip2 detection circuit 186 detects the second pumping current Ip2.

The heater drive circuit 187 applies a positive voltage for energizing the heater 160 to one end of the heater 160, which is a heat-generating resistor, and applies a negative voltage for energizing the heater 160 to the other end of the heater 160 to thereby drive the heater 160.

The electromotive force detection circuit 188 detects the electromotive force between the reference electrode 212 and the detection electrode 214 (hereinafter referred to as an ammonia electromotive force EMF) and outputs a signal representing the detection result to the microcomputer 190.

The microcomputer 190 includes a CPU 191, a ROM 192, a RAM 193, and a signal input/output unit 194.

The CPU 191 executes a process for controlling the sensor element unit 5 according to a program stored in the ROM 192. The signal input/output unit 194 is connected to the Ip1 drive circuit 181, the Vs detection circuit 182, the Ip2 detection circuit 186, the heater drive circuit 187, and the electromotive force detection circuit 188. The CPU 191 outputs a driving signal to the heater drive circuit 187 through the signal input/output unit 194 to control the heater 160.

The CPU 191 executes a process for removing the influence of the oxygen concentration from the value of the second pumping current Ip2 and from the ammonia electromotive force EMF on the basis of various data stored in the ROM 192 and further executes a process for computing NOx concentrations such as the concentration of NO and the concentration of $NO_2$ and the concentration of ammonia. No particular limitation is imposed on these processes, and processes described in, for example, Japanese Patent Application Laid-Open (kokai) No. 2011-075546 may be used.

The above-configured ammonia detection section 102 is disposed on the electrically insulating layer 120 and has a structure including the reference electrode 212, the solid electrolyte body 213 for ammonia, and the detection electrode 214 that are stacked in this order on the insulating layer 120. In the ammonia detection section 102, a three-phase boundary is formed at the interface between the reference electrode 212 and the solid electrolyte body 213 for ammonia, and another three-phase boundary is formed at the interface between the detection electrode 214 and the solid electrolyte body 213 for ammonia. The concentration of ammonia in the exhaust gas is thereby detected.

The ammonia detection section 102 includes the porous layer 211 formed of an electrically insulating porous material and disposed between the insulating layer 120 and the reference electrode 212.

In the above-configured ammonia detection section 102, the porous layer 211 is disposed on the opposite side of the reference electrode 212 from the solid electrolyte body 213 for ammonia. The porous layer 211 has many pores in its interior and on its surface. Therefore, in the porous layer 211, ammonia is allowed to flow from a portion exposed to the exhaust gas into the interior of the porous layer 211, and the ammonia flowing inside the porous layer 211 is allowed to flow toward the reference electrode 212.

Therefore, the amount of ammonia flowing through the reference electrode 212 toward the solid electrolyte body 213 for ammonia increases, and this allows an increase in the area of the three-phase boundary at which ammonia comes into contact with the reference electrode 212 and the solid electrolyte body 213 for ammonia. When a stack of the reference electrode 212 and the solid electrolyte body 213 for ammonia is formed on a green insulating layer 120 and then they are co-fired, the reference electrode 212 may become dense, and the area of the three-phase boundary may decrease. Even in this case, the increase in the inflow of ammonia through the porous layer 211 allows the reduction in the area of the three-phase boundary to be suppressed.

In the ammonia detection section 102, the rise in impedance of the ammonia detection section 102 due to co-firing can be suppressed in the manner described above.

Figure 3:
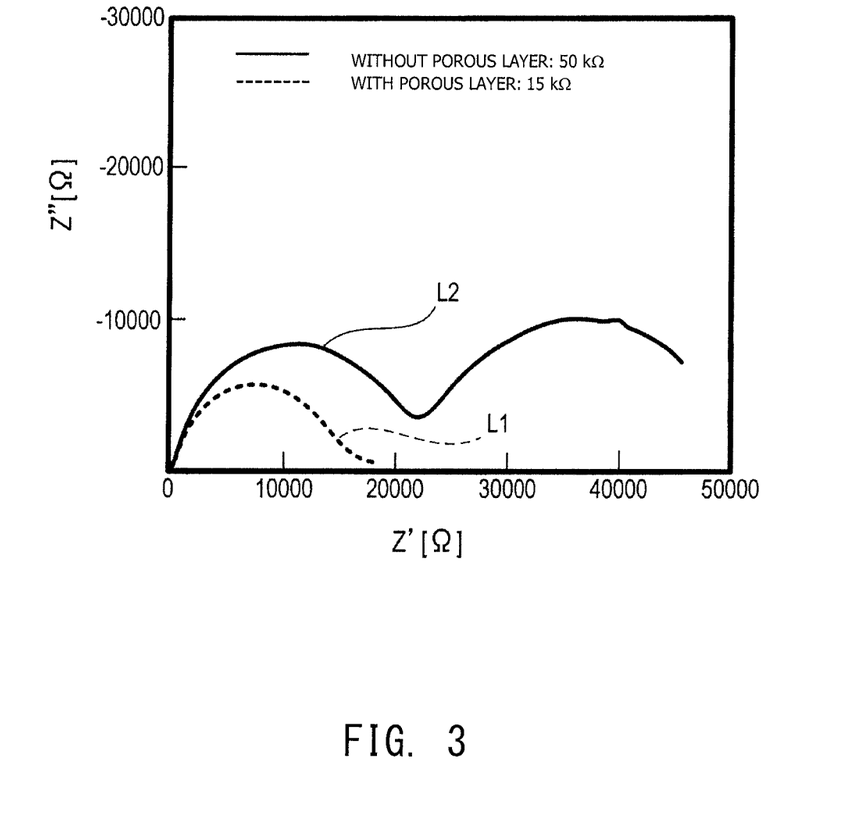
FIG. 3 is a complex impedance plot showing the difference in impedance between structures with and without a porous layer.
Figure 4A:
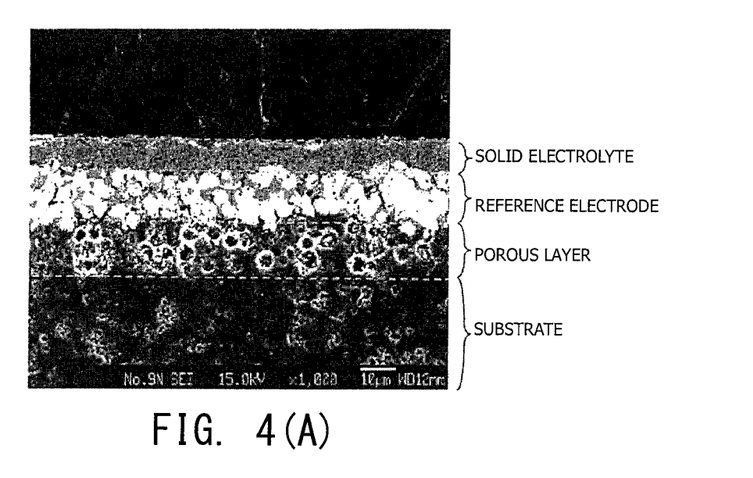
FIGS. 4(A) and 4(B) are cross-sectional views showing the difference between the structures with and without the porous layer.
Figure 4B:
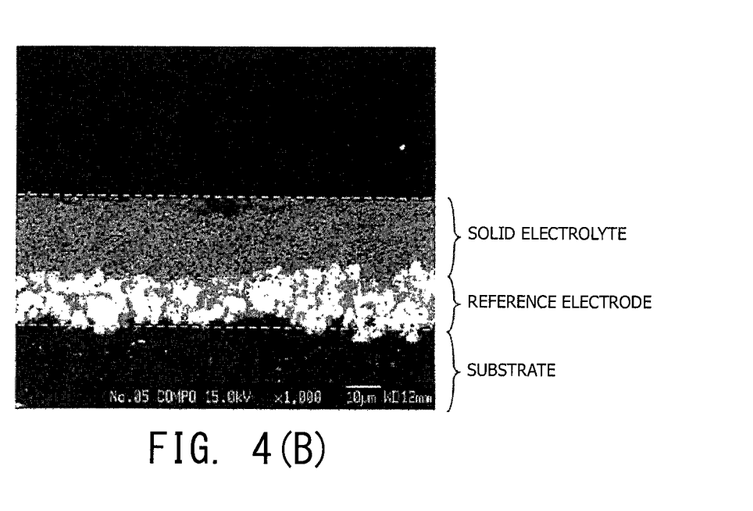

FIG. 3 is a complex impedance plot for a structure prepared by stacking a porous layer, a reference electrode, and a solid electrolyte body on a substrate as shown in FIG. 4(A) and for a structure prepared by stacking a reference electrode and a solid electrolyte body on a substrate as shown in FIG. 4(B). A curve L1 in FIG. 3 is a complex impedance plot for the structure shown in FIG. 4(A), and a curve L2 in FIG. 3 is a complex impedance plot for the structure shown in FIG. 4(B).

As shown in FIG. 3, by disposing the porous layer between the substrate and the reference electrode, the impedance can be reduced.

In the embodiment described above, the ammonia detection section 102 is the gas sensor of the first aspect of the present invention, and the insulating layer 120 is the insulating member in the first aspect. The solid electrolyte body 213 for ammonia is the solid electrolyte body in the first aspect, and the porous layer 211 is the insulating porous layer in the first aspect.

The exhaust gas is the atmosphere of interest in the first aspect, and ammonia is the detection target gas in the first aspect.

Second Embodiment

A second embodiment of the present invention will next be described with reference to FIG. 5. In the second embodiment, differences from the first embodiment will be described. The same reference numerals as those in the first embodiment indicate the same components, and their description will be omitted.

A multi-gas detector 1 in the second embodiment is different from the multi-gas detector 1 in the first embodiment in that an ammonia detection section 302 is provided instead of the ammonia detection section 102.

Figure 5:
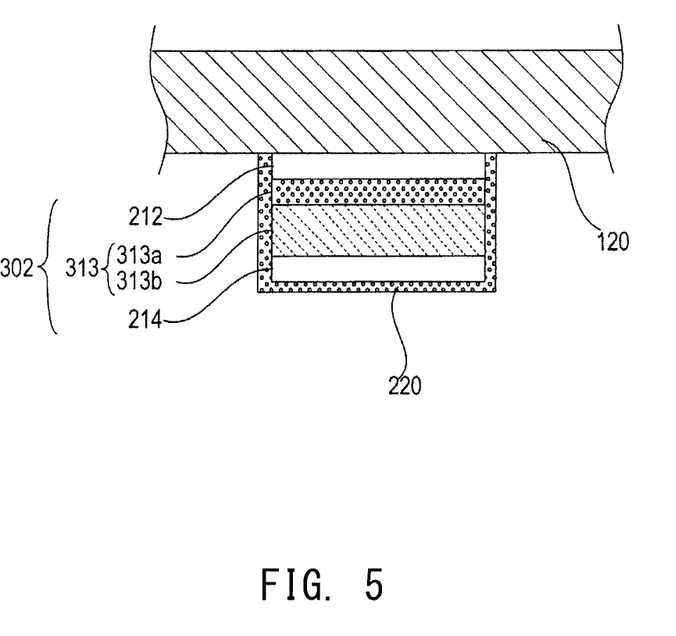
FIG. 5 is an illustration showing the schematic structure of an ammonia detection section 302.

As shown in FIG. 5, the ammonia detection section 302 is formed on the insulating layer 120 and has a structure including the reference electrode 212, a solid electrolyte body 313 for ammonia, and the detection electrode 214 that are stacked in this order.

The solid electrolyte body 313 for ammonia includes a porous layer 313a and a non-porous layer 313b.

The porous layer 313a is a porous layer formed of the same material as the material of the solid electrolyte body 213 for ammonia (i.e., an oxygen ion-conductive material such as yttria-stabilized zirconia (YSZ)) and is formed on the reference electrode 212.

The non-porous layer 313b is a non-porous layer formed of the same material as the material of the solid electrolyte body 213 for ammonia and is formed on the porous layer 313a.

The above-configured ammonia detection section 302 is disposed on the electrically insulating layer 120 and has a structure including the reference electrode 212, the solid electrolyte body 313 for ammonia, and the detection electrode 214 that are stacked in this order on the insulating layer 120. In the ammonia detection section 302, a three-phase boundary is formed at the interface between the reference electrode 212 and the solid electrolyte body 313 for ammonia, and another three-phase boundary is formed at the interface between the detection electrode 214 and the solid electrolyte body 313 for ammonia. The concentration of ammonia in the exhaust gas is thereby detected.

In the ammonia detection section 302, a portion of the solid electrolyte body 313 for ammonia that is in contact with the reference electrode 212 is porous.

As described above, in the ammonia detection section 302, the porous layer 313a is disposed between the non-porous layer 313b and the reference electrode 212. Therefore, in the porous layer 313a, ammonia is allowed to flow from a portion 313a exposed to the exhaust gas into the interior of the porous layer 313a, and the ammonia flowing inside the porous layer 313a is allowed to flow toward the reference electrode 212.

Therefore, the amount of ammonia flowing through the solid electrolyte body 313 for ammonia toward the reference electrode 212 increases, and this allows an increase in the area of the three-phase boundary at which ammonia comes into contact with the reference electrode 212 and the solid electrolyte body 313 for ammonia. When a stack of the reference electrode 212 and the solid electrolyte body 313 for ammonia is formed on a green insulating layer 120 and then they are co-fired, the reference electrode 212 may become dense, and the area of the three-phase boundary may decrease. Even in this case, the increase in the inflow of ammonia through the porous layer 313a allows the reduction in the area of the three-phase boundary to be suppressed.

In the ammonia detection section 302, the rise in impedance of the ammonia detection section 302 due to co-firing can be suppressed in the manner described above.

In the embodiment described above, the ammonia detection section 302 is the gas sensor of the second aspect of the present invention, and the solid electrolyte body 313 for ammonia is the solid electrolyte body in the second aspect.

While the embodiments of the present invention have been described, the present invention is not limited to these embodiments. The present invention can be implemented in various forms so long as they fall within the technical scope of the invention.

For example, in one of the embodiments, the ammonia detection section 102 having a stacked structure including the reference electrode 212, the solid electrolyte body 213 for ammonia, and the detection electrode 214 detects the concentration of ammonia. However, the present invention is not limited to the gas sensor that detects the concentration of ammonia. Specifically, the present invention is applicable to any gas sensor for detecting the concentration of a gas other than ammonia, so long as the gas sensor has a stacked structure including a reference electrode, a solid electrolyte body, and a detection electrode.

In one of the embodiments, the ammonia detection section 102 is formed on the outer surface of the NOx detection section 101. However, the present invention is not limited to the ammonia detection section formed on the gas sensor. The ammonia detection section 102 may be formed on any electrically insulating member.

DESCRIPTION OF REFERENCE NUMERALS

1: multi-gas detector, 2: multi-gas sensor, 3: controller, 5: sensor element unit, 101: NOx detection section, 102: ammonia detection section, 120: insulating layer, 211: porous layer, 212: reference electrode, 213: solid electrolyte body for ammonia, 214: detection electrode, 302: ammonia detection section, 313: solid electrolyte body for ammonia, 313*a*: porous layer, and 313*b*: non-porous layer.

The invention claimed is:

1. A gas sensor disposed on an electrically insulating member for detecting the concentration of a target gas in an atmosphere of interest, said gas sensor comprising:
    a reference electrode;
    a solid electrolyte body;
    a detection electrode; and
    an insulating porous layer, wherein
    the reference electrode, the solid electrolyte body, and the detection electrode are stacked in this order on the electrically insulating member,
    a first three-phase boundary is formed at a first interface between the reference electrode and the solid electrolyte body,
    a second three-phase boundary is formed at a second interface between the detection electrode and the solid electrolyte body, and
    the insulating porous layer is made of an electrically insulating porous material and is disposed between the electrically insulating member and the reference electrode.

2. The gas sensor according to claim 1, wherein the insulating porous layer abuts the reference electrode.

3. The gas sensor according to claim 1, wherein the target gas flows into the reference electrode through the insulating porous layer.

4. The gas sensor according to claim 1, wherein the target gas is ammonia.

5. The gas sensor according to claim 1, wherein
    the first three-phase boundary is a boundary at which the target gas contacts the reference electrode and the solid electrolyte body, and
    the second three-phase boundary is a boundary at which the target gas contacts the detection electrode and the solid electrolyte body.

6. A gas sensor disposed on an electrically insulating member for detecting the concentration of a target gas in an atmosphere of interest, said gas sensor comprising:
    a reference electrode;
    a solid electrolyte body; and
    a detection electrode, wherein
    the reference electrode, the solid electrolyte body, and the detection electrode are stacked in this order on the electrically insulating member,
    a first three-phase boundary is formed at a first interface between the reference electrode and the solid electrolyte body,
    a second three-phase boundary being formed at a second interface between the detection electrode and the solid electrolyte body,
    at least part of the solid electrolyte body is porous and forms a porous part that abuts the reference electrode, and
    the target gas flows into the reference electrode through the porous part of the solid electrolyte body.

7. The gas sensor according to claim 6, wherein the electrically insulating member abuts the reference electrode.

8. The gas sensor according to claim 6, wherein the target gas is ammonia.

9. The gas sensor according to claim 6, wherein
    the first three-phase boundary is a boundary at which the target gas contacts the reference electrode and the solid electrolyte body, and
    the second three-phase boundary is a boundary at which the target gas contacts the detection electrode and the solid electrolyte body.

* * * * *